United States Patent
Granzow

(10) Patent No.: US 10,031,127 B2
(45) Date of Patent: Jul. 24, 2018

(54) METHOD FOR SEPARATING AGGREGATES OF MALIGNANT CELLS AND AGGREGATES FROM STROMAL CELLS OF A MALIGNANT TUMOUR TISSUE SAMPLE

(71) Applicant: Flacod GmbH, Heidelberg (DE)

(72) Inventor: Christof Granzow, Heidelberg (DE)

(73) Assignee: FLACOD GmbH, Heidelberg (DE)

( * ) Notice: Subject to any disclaimer, the term of this patent is extended or adjusted under 35 U.S.C. 154(b) by 750 days.

(21) Appl. No.: 14/372,243

(22) PCT Filed: Jan. 28, 2013

(86) PCT No.: PCT/DE2013/000046
§ 371 (c)(1),
(2) Date: Jul. 15, 2014

(87) PCT Pub. No.: WO2013/127376
PCT Pub. Date: Sep. 6, 2013

(65) Prior Publication Data
US 2015/0004642 A1 Jan. 1, 2015

(30) Foreign Application Priority Data
Feb. 28, 2012 (DE) .......... 10 2012 003 700

(51) Int. Cl.
*G01N 33/50* (2006.01)
*C12N 5/00* (2006.01)

(52) U.S. Cl.
CPC ....... *G01N 33/5011* (2013.01); *C12N 5/0093* (2013.01); *G01N 2500/10* (2013.01)

(58) Field of Classification Search
CPC ........... G01N 2500/10; G01N 33/5005; G01N 33/5008; G01N 33/5044; Y10S 435/842
See application file for complete search history.

(56) References Cited

U.S. PATENT DOCUMENTS

| | | | | |
|---|---|---|---|---|
| 5,261,410 A * | 11/1993 | Alfano | ................. | A61B 5/0075 250/339.12 |
| 6,008,047 A * | 12/1999 | Curcio | ................. | C12N 5/0617 424/93.7 |
| 6,872,567 B2 * | 3/2005 | Thomas | ................. | C07K 16/28 435/2 |
| 2001/0051353 A1 | 12/2001 | Kornblith | | |
| 2003/0096261 A1 | 5/2003 | Fruehauf et al. | | |
| 2007/0292389 A1 * | 12/2007 | Stassi | ................. | C12N 5/0695 424/85.2 |

FOREIGN PATENT DOCUMENTS

| | | |
|---|---|---|
| WO | 2004/052184 A2 | 6/2004 |
| WO | 2009/124997 A1 | 10/2009 |

OTHER PUBLICATIONS

Thermo Scientific. Thermo scientific finnpipette finntip. Thermo Scientific. 2010;1-24.*
Worthington. Dissociating enzymes: collagenase. Worthington Tissue Dissociation Guide. 2008;1-2.*
Dollner R, Granzow C, Helmke BM, Ruess A, Schad A, Dietz A: The impact of stromal cell contamination on chemosensitivity testing of head and neck carcinoma. Anticancer Res. 24, (2004), pp. 325-31.
Granzow C, Kopun M, Heuser M, Herth F, Becker HD: Chemoresistance of human lung tumor stromal cells. Amer. Assn. Cancer Res. 95th Annual Meeting Proc. Suppl., abstract LB-82, (2004), pp. 74-75.
Kerbel R S: A cancer therapy resistant to resistance. Nature 390, (1997), p. 335-336.
Patti A, Dressman HK, Bild A, Riedel RF, Chan G, Sayer R, Cragun J, Cottrill H, Kelley MJ, Petersen R, Harpole D, Marks J, Berchuck A, Ginsburg GS, Febbo P, Lancaster J, Nevins JR.: Genomic signatures to guide the use of chemotherapeutics. Nat. Med. Volume 12, No. 11, (Nov. 2006), pp. 1294-1300.
Iris-Susanne Horn et al: "Heterogeneity of epithelial and stromal cells of head and neck squamous cell carcinomas in ex vivo chemoresponse", Cancer Chemotherapy and Pharmacology, Springer, Berlin, DE, vol. 65, No. 6, Sep. 22, 2009, pp. 1153-1163, XP019800787, ISSN: 1432-0843.
International Search Report of PCT/DE2013/000046, dated May 19, 2014.
Baker, N. et al. "Identification of stem cells in small intestine and colon by marker gene Lgr5." Nature. Oct. 25, 2007;449(7165):1003-7. Epub Oct. 14, 2007.

* cited by examiner

*Primary Examiner* — Lynn Y Fan
(74) *Attorney, Agent, or Firm* — Collard & Roe, P.C.

(57) ABSTRACT

An ex vivo malignant tumor tissue sample is cleaned, comminuted, suspended in culture medium, subjected to a treatment with collagenase and the collagenase decomposition product is centrifuged. The pellet obtained is re-suspended in culture medium by an absorption instrument, is absorbed and returned several times and transferred to a culture vessel. The re-suspension thus obtained is analyzed under a microscope with phase optics for cell aggregates, which, due to the phenotypic appearance thereof, are identifiable as an aggregate of malignant cells or as an aggregate of endothelial cells or as an aggregate of fibroblasts, and the identified cell aggregates are separated.

10 Claims, 1 Drawing Sheet

Figure 1:
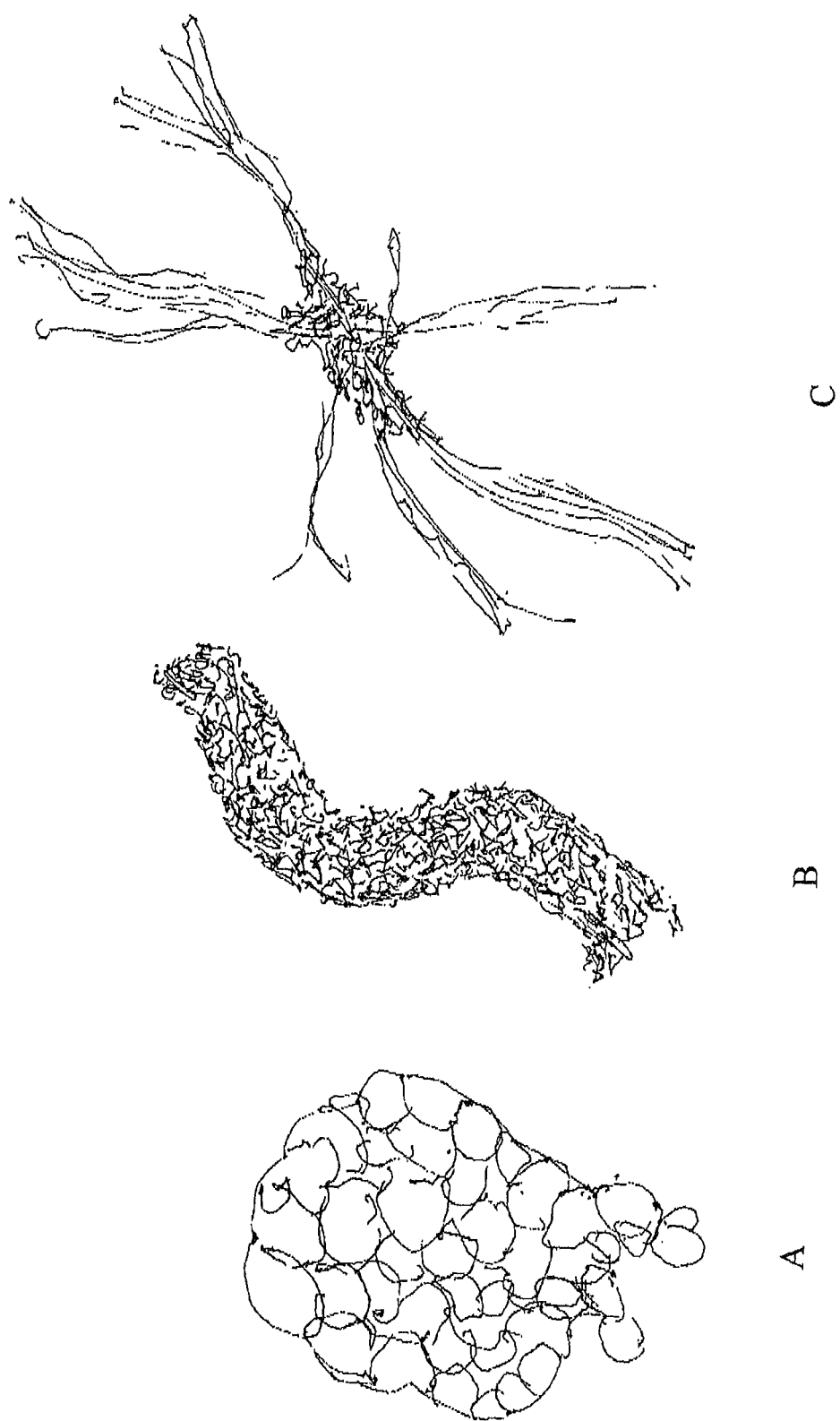

METHOD FOR SEPARATING AGGREGATES OF MALIGNANT CELLS AND AGGREGATES FROM STROMAL CELLS OF A MALIGNANT TUMOUR TISSUE SAMPLE

CROSS REFERENCE TO RELATED APPLICATIONS

This application is the National Stage of PCT/DE2013/000046 filed on Jan. 28, 2013, which claims priority under 35 U.S.C. § 119 of German Application No. 10 2012 003 700.7 filed on Feb. 28, 2012, the disclosures of which are incorporated by reference. The international application under PCT article 21(2) was not published in English.

The invention relates to a method for separating clusters of malignant cells and clusters of stromal cells of a malignant tumor tissue sample ex vivo.

Malignancies (synonym: cancer tumors) are malignant tumors that escape the normal control by the body so they reproduce to an unlimited extent, penetrate into surrounding tissue and destroy it. These tumors can metastasize, i.e., they can invade the blood vessels and lymphatic vessels, through which they can reach other organs of the body, where they settle and multiply reproduce (i.e., form metastases).

On the other hand, benign tumors are characterized in that they do not grow invasively into the surrounding tissue but instead merely displace it and do not form any metastases.

Carcinomas account for by far the majority of malignant tumors. Carcinomas are malignant tumors that start from epithelial cells (the surface epithelium of the skin or the glandular epithelium of the mucous membranes). Epithelial cells normally have a polarized structure: they have basolateral sides which connect the cells to one another by way of intercellular connecting structures (e.g., desmosomes, tight junctions, adherent junctions), a basal side to the extracellular matrix, which has specific cell membrane proteins and the basal membrane, and an apical side, which is connected to the lumen, i.e., the surrounding environment. The integrity of the epithelial cells is supported by the connective tissue which contains the blood vessels and fibroblasts.

In the development of carcinomas, the cellular organization of the epithelium mutates. It is assumed that most carcinomas are caused by individual malignant cells (precursor cells) which grow to form a cell clone and ultimately form a tumor. This growth is associated with numerous changes in the environment of the malignant cells, including neoangiogenesis, to ensure a supply of nutrients and oxygen and others to the malignant tumor.

The tissue surrounding the malignant cells, the so-called tumor stroma, has a significant influence on the growth of the malignant tumor on both a cellular level and an extracellular level. This tumor stroma consists of neighbouring cells, in particular endothelial cells and fibroblasts (Kerbel, 1997), and of extracellular matrix, and both these neighbouring cells and the matrix differ from the corresponding cells and the matrix in healthy tissue with regard to their components.

Although treatment with radiation or administration of cytostatic drugs or with a combination of both methods have been used for decades in the treatment of malignant tumors (synonym: cancer therapy), the success rate with most carcinomas is still only about 20 percent.

With chemotherapy in particular there is the problem that treatment with an inappropriate (wrong) chemotherapeutic drug or in a dosage that is too low not only fails to have a malignancy-inhibiting effect but also can lead to an increased therapeutic resistance of the malignant tumor. In the case of two or more chemotherapy cycles with the same chemotherapeutic drug, which is a standard measure in the state of the art, the success rates after the second treatment and additional treatments are therefore usually much lower than those after the first treatment.

At the present time most treatment plans in chemotherapy and radiation therapy are more or less defined empirically, which is problematic because each malignant tumor in an individual patient will respond individually to a chemotherapeutic agent and/or radiation.

However test methods have already been proposed, for effective treatment of an individual and directed/tailored to the specific individual malignant tumor, and these test methods can be used to test the sensitivity of the malignant cells to the planned therapeutic agent, in particular the chemotherapeutic agent, before administering a planned chemotherapy and/or radiotherapy. Such a test procedure is performed ex vivo on a freshly isolated malignant tumor tissue sample. The term "ex vivo" refers to a cell culture technique (in the context of the present description) using tissue samples taken freshly from the body. (From such tissue samples the so-called primary (cell) cultures are prepared, for example, which are usually cellularly inhomogeneous). This malignant tumor tissue sample is first minced and more or less completely broken up into individual cells, which are then incubated with the therapeutic agent in question, and next the growth behaviour of the cells treated in this way is determined. By incubating with various concentrations of the therapeutic agent, its IC50 value can be determined. The IC50 value of a chemotherapeutic agent stands for the concentration of the agent at which the proliferation of the cells treated with that agent and tested is reduced to 50% in comparison with the untreated control cells. The IC50 value is an important criterion for the description of the reaction of a malignant tumor to a chemotherapeutic agent.

On the basis of the test results, it is possible to predict how sensitive the malignant tumor will be to the therapeutic agent and how the treatment plan should consequently be designed with respect to dosage and administration cycles in order to achieve the desired malignancy-inhibiting or malignancy-destroying effect. Such test methods are described in US 2001/0051353 A1 and in WO 2009/124997 A1, for example.

With respect to the cellular chemoresponse (i.e., the cellular response to a certain chemotherapeutic agent), the accepted learned opinion is that only the malignant cells of a malignant tumor are capable of developing a resistance, but the stromal cells of a malignant tumor are not (Kerbel, 1997). However, in recent years a chemoresistance has also been detected in the stromal cells of malignant tumors, for example, in primary and metastatic lung carcinomas (Granzow et al., 2004) and in carcinomas of the head and neck (Dollner et al., 2004). With these both aforementioned carcinoma entities, malignant tumors with chemoresistant malignant cells and chemoresistant stromal cells have been detected as well as malignant tumors with chemosensitive malignant cells and chemosensitive stromal cells, as well as malignant tumors with chemosensitive malignant cells and chemoresistant stromal cells and also malignant tumors with chemoresistant malignant cells and chemosensitive stromal cells. The identification and testing of the various cell types in these detections were each performed by using samples of human malignant tumors ex vivo in suitable cell culture dishes where the aforementioned types of cells were co-cultured in the presence or absence of cytostatic drugs (Dietz et al, 2009).

From this finding that in a malignant tumor, stromal cells and malignant cells may have very different sensitivities to a certain therapeutic agent independently of one another, it follows that the known test methods described above for testing malignant cells of a malignant tumor tissue sample (from a patient) for their sensitivity to a therapeutic agent intended to be administered, in particular a chemotherapeutic agent, it will not be unusual for them to deliver false-negative or false-positive results.

The result of a molecular analysis of the gene expression profile with regard to chemoresistance genes (analysis of molecular tumor chemoresponse signatures) performed with such a malignant tumor tissue sample can also be falsified due to the fact that chemosensitive stromal cells may coexist with chemoresistant malignant cells.

Therefore the object of the present invention is to overcome or at least ameliorate these disadvantages of the prior art.

One solution to this problem consists of providing a method for separating clusters of malignant cells and clusters of stromal cells (in particular endothelial cells and fibroblasts) of an ex vivo malignant tumor tissue sample in which the tumor tissue sample (preferably obtained freshly) is:

(a) first (preferably within 9 minutes at most) purified to remove necrotic components and adhering other (nonmalignant) tissue and minced (preferably chopped), preferably into pieces with a volume of approximately 1 to 4 mm$^3$ (cubic millimeters), (b) the minced tissue is suspended in a culture medium (preferably containing serum), (c) the suspension thereby obtained is subjected to a treatment with collagenase (i.e., a collagenase digestion or a collagenase decomposition, respectively) at approximately 36° C. to 37° C., (d) the collagenase decomposition product thereby obtained is centrifuged, preferably for a period of approximately 5 minutes at 50×g at room temperature, and (e) the pellet thereby obtained is separated from the supernatant.

This method is characterized according to the invention in that the measures and/or steps (f), (g) and (h) follow (e), namely:

(f) the pellet obtained at the end of step (e) is decomposed and resuspended in culture medium by means of an aspiration device (for example, a pipette tip), thereby quickly aspirated, returned (allowed to flow back into the dish) and drawn in again for several times, preferably about 4-6 times, and finally transferred to a culture vessel.

(g) The resuspension obtained in (f), by repeatedly aspirating and re-dispensing, is analysed with the help of a microscope (preferably using an inverse microscope equipped with a phase contrast lens system) with regard to at least one cell cluster each, that either can be identified on the basis of its phenotypic appearance as a cluster of malignant cells, or that can be identified on the basis of its phenotypic appearance as a cluster of endothelial cells, or that can be identified on the basis of its phenotypic appearance as a cluster of fibroblasts.

The cell clusters of malignant cells are characterized phenotypically by an approximately roundish shape of the cell cluster, by cells with relatively large diameter and high phase contrast, and by compact close arrangement of the cells in this cell cluster. On the other hand, the clusters of stromal cells in the case of endothelial cells are characterized phenotypically by cells with an apparently smaller size and a lower phase contrast in comparison with the malignant cells in the cell clusters, and by a densely packed agglomeration in the form of convoluted elongated tubes. In the case of fibroblasts, the clusters of stromal cells are characterized phenotypically by a smaller cell size in comparison with the malignant cells in the cell cluster and by close association with partially digested collagen fibre bundles.

(h) The cell clusters identified in (g) are separated, for example, by transferring them to separate culture vessels or test vessels.

Here and below the term "malignant cells" stands for those cells of a malignant tumor that proliferate autonomously, are capable of invasive destructive growth and can form metastases.

The term "stromal cells" here and below stands first for those cells of a malignant tumor that co-proliferate with the malignant cells but do not have a biological malignancy. These stromal cells are mainly fibroblasts and cellular components of the vascular system, in particular endothelial cells. Secondly, the term "stromal cells" also includes all the nonmalignant cells in a malignant tumor that are not capable of ex vivo proliferation.

The term "cell cluster" (plural: "cell clusters") here and below stands for pre-existing (i.e., originally already present/existent), cellularly largely homogeneous aggregations of cells, for example of malignant cells, fibroblasts or endothelial cells, in the tissue of a malignant tumor, which are released as a result of the action of collagenase and shearing forces (during aspiration into and re-release out of the aspiration device).

The abbreviation "g" stands for the mean acceleration due to the earth's gravity.

The method according to the invention is associated with the advantages that the partial collagenase digestion followed by a brief mild hydromechanical treatment (involving shearing forces) leads to the formation of isolated cell clusters, which consist either of malignant cells or of one of the types of stromal cells, i.e., fibroblasts or endothelial cells, and can be identified and separated easily on the basis of their phenotypic appearance. The malignant cells in particular are obtained largely in their original state (i.e., the condition in the malignant tumor in vivo). In the case of carcinoma cells, for example, the cell clusters consist of individual cells which belong together phenotypic and are coordinated with one another and are in contact with one another by way of cell-bonding structures (for example, desmosomes).

Thus the malignant cells can be isolated rapidly, inexpensively and in a technically uncomplicated manner from the malignant tumor tissue sample originally obtained, and then only these malignant cells are subjected to a test method to test their sensitivity for a certain chemotherapeutic agent or radiotherapy intended for use.

The freshly obtained malignant tumor tissue sample may have been obtained in particular as part of a resection or biopsy.

In the method according to the invention, the collagenase used is preferably *Clostridium histolyticum* collagenase, which is used for a period of about 4 to 5 hours, because a relatively mild, only partial collagenase digestion can be performed by this way. The period of time should preferably not exceed 5 hours. The amount of collagenase used is preferably about 200 CDU to 250 CDU per mL, but very good results can be obtained in particular with approximately 230 CDU/mL.

In step (h) of the method, the resuspension can be analysed with regard to cell clusters of malignant cells and also with regard to cell clusters of fibroblasts and/or cell clusters of endothelial cells, and the cell clusters that have been identified can be isolated, for example, by absorbing them separately (individually) with the help of an aspiration device and transferring each cluster to a separate culture vessel. An injection cannula no. 23 (diameter 0.6 mm, length 60-80 mm) in particular can be attached to a 2 mL injection syringe for use as the aspiration device.

If desired, only identified cell clusters of endothelial cells and/or only identified cell clusters of fibroblasts can be taken from the resuspension—, for example because they are to be subjected to more extensive testing. According to the invention a method for testing the effect of inhibiting substances of angioneogenesis on the separated cell clusters of endothelial cells may be particularly considered as one such more extensive test.

Alternatively, all the identified cell clusters of endothelial cells and all the cell clusters of fibroblasts can be taken from the resuspension so that only malignant cells remain. The cellularly homogenous or at least mostly homogeneous suspension of malignant cells in culture medium thus obtained is available for more extensive testing of the malignant cells and has the advantage that the malignant cells were subjected only once to the suction treatment and the hydrodynamic (shearing) forces associated therewith.

In one variant of the method according to the invention, the various cell clusters contained in the resuspension are separated in step (g) by means of density gradient centrifugation on the basis of their different sedimentation behaviour. For this purpose, the resuspension obtained in (f) is transferred to a separation solution of sucrose polymer in a culture medium. Sucrose-epichlorohydrin copolymer, (e.g. Ficoll®) is preferably used as the sucrose polymer. In the course of this density gradient centrifugation, the clusters of malignant cells will sediment out at higher concentrations of the sucrose polymer, in particular the sucrose-epichlorohydrin copolymer, than the clusters of fibroblasts or the clusters of endothelial cells.

Instead of density gradient centrifugation, centrifugal elutriation may also be performed. For this purpose the resuspension obtained in (f) is transferred to a separation chamber for centrifugal elutriation, which is known in the prior art, and then is elutriated, whereupon the clusters of malignant cells collect at higher flow rates than the clusters of stromal cells.

The method according to the invention is also provided according to the invention as a precursor method for a method for evaluating/checking the response of malignant cells of a malignant tumor tissue sample ex vivo to a known chemotherapeutic agent and/or radiotherapy. In other words, the method according to the invention is provided in particular for preparing (or pretreating or conditioning) malignant tumor tissue samples ex vivo for a method for testing their sensitivity and possible resistance to a known chemotherapeutic agent and/or radiotherapeutic agent.

The method for testing the sensitivity and possible resistance to a known chemotherapeutic agent and/or radiotherapeutic agent (radiation therapy) may be a cell growth test, in which the cells are incubated and/or treated with the chemotherapeutic agent and/or the radiotherapeutic agent (known in the prior art from US 2001/0051353 A1 and WO 2009/124997 A1, for example), or it may be a method for molecular analysis of the gene expression profile. Such methods for molecular analysis of the gene expression profile are known in the prior art, for example, from Potti et al., 2006.

The subject matter of the invention therefore comprises further a method for evaluation/testing of the growth-inhibiting effect of a known chemotherapeutic agent and/or radiotherapeutic agent on a malignant tumor tissue sample ex vivo, in which the malignant tumor tissue sample is exposed to a chemotherapeutic and/or radiotherapeutic agent, and then the number of cells and/or cell colonies is analysed, and finally, the IC50 value of the chemotherapeutic or radiotherapeutic agent or of the combination of chemotherapeutic and radiotherapeutic agent is determined. This method is characterized in that the malignant tumor tissue sample is digested to yield malignant cells and stromal cells before being incubated with the chemotherapeutic and/or radiotherapeutic agent, and that only malignant cells are exposed to the chemotherapeutic and/or radiotherapeutic agent and are analysed with regard to the IC50 value.

The term radiotherapeutic agent in the present context in particular stands for ionizing radiation.

In other words, it is proposed according to the invention that the ex vivo malignant cell sample must first be subjected to a method for separating malignant cells and stromal cells, preferably the method according to the invention, and then only the separated malignant cells are to be used in a method for molecular analysis of the gene expression profile and/or in a method for evaluation/testing for sensitivity and/or resistance to a selected presumed chemotherapeutic and/or radiotherapeutic agent.

Said method for evaluating/testing a malignant tumor tissue sample for sensitivity and/or resistance to a known presumed chemotherapeutic and/or radiotherapeutic agent may be in particular an ex vivo method comprising of the following measures:

A freshly isolated malignant tumor tissue sample is transferred to a container and kept at a temperature of more than 10° C., preferably more than 15° C. in the presence of antibiotics and preferably also antimycotics.

The malignant tumor tissue sample is split up into small pieces, preferably mechanically.

The malignant tumor tissue sample pieces are transferred within max. 12 hours, preferably within 5 hours after the start of the method to cell culture medium with a collagenase content and then incubated there for at least 10 hours, then washed and resuspended in cell culture medium.

The cells and tissue parts thereby obtained are transferred to containers with a coating of extracellular matrix components, plated out on this coating and incubated with the chemotherapeutic and/or radiotherapeutic agent.

Next the number of cells and/or the number of colonies is analysed, preferably after performing a cytokeratin staining.

The cell culture medium used contains less than 100 nmol per 1 liter flavin and is free of phenol red.

All the measures following the collagenase treatment are performed in the absence of light of a wavelength of less than 520 nm.

The IC50 value is determined for the chemotherapeutic or radiotherapeutic agent or for the combination of a chemotherapeutic agent and a radiotherapeutic agent.

If this method for testing a malignant tumor tissue sample for sensitivity or resistance to a known presumed chemotherapeutic and/or radiotherapeutic agent is combined with the method according to the invention for separation of malignant cells and stromal cells, then the separation method according to the invention replaces the aforementioned first (three) steps up to and including the collagenase treatment of this test method.

The invention will be explained in greater detail on the basis of the following exemplary embodiments and the respective figures:

FIG. 1 shows: a schematic diagram of the phase-optical image of a cluster of malignant cells (A), of a cluster of endothelial cells (B), and of a-cluster of fiber-associated fibroblasts (C), each obtained with the method according to the invention.

EXAMPLE 1: SEPARATION OF MALIGNANT CELLS AND OF STROMAL CELLS FROM TISSUE SAMPLES OF MALIGNANT LUNG TUMORS

Samples were freshly resected from malignant lung tumors of various histologies, then purified and minced. Tumor tissue samples of 5 to 10 mg per 1 mL were suspended in RPMI 1640 culture medium with an FBS content of 10%. These suspensions were subjected to a collagenase digestion, preferably using *Clostridium histolyticum* collagenase (230 CDU/mL) for a period of 4 to 5 hours at 36° C. to 37° C., preferably at 36.5° C. Next the digested product was centrifuged at 50×g, the supernatant was discarded and the pellet was dissolved and resuspended in 1 mL fresh culture medium. Each test preparation was transferred to a Petri dish and adjusted with culture medium to a concentration corresponding to 5 to 10 mg tumor sample wet weight per 1 mL culture medium.

The cell suspension of each test preparation (test run) was picked up with a 1 mL pipette tip (another aspiration device can also be used) and then discharged again, 4 to 5 times in succession, and thereby subjected to a treatment with hydrodynamic shearing forces. Next, with the help of an inverse microscope equipped with a phase contrast lens system, cell clusters of phenotypically the same cells were detected and each was transferred to a separate culture vessel using injection cannulas no. 23 (diameter 0.6 mm, length 60-80 mm) attached to 2 mL injection syringes.

The purity of the cell clusters obtained in this way was tested by means of phase contrast microscopy.

Samples (preparations) of these cell clusters as well as of the unfractionated digestion products were tested for their chemosensitivity to cisplatin. To do so, the samples (preparations) were incubated in culture plates coated with extracellular matrix (ECM) for 3 days in the presence of 0 nM, 60 nM, 600 nM and 6000 nM cisplatin. Next the cells were fixed with methanol, subjected to a Giemsa staining or an immune staining with an anti-cytokeratin antibody (for example, the antibody C11) and finally analysed microscopically.

The microscopic phase-optical analysis of the digestion products revealed that co-existing stable clusters of spatially closely associated cells can be distinguished therein, said cells being either malignant cells or endothelial cells or fiber-associated fibroblasts. Clusters of malignant cells appear round or roundish under a phase-contrast microscope. Their cells have relatively large diameters and a high phase contrast and are densely packed (cf. FIG. 1 A). Such cell clusters sediment rapidly. Clusters of endothelial cells form convoluted tubes reminiscent of blood vessels. The endothelial cells themselves appear smaller in comparison with the malignant cells, have a lower phase contrast and are densely packed (cf. FIG. 1 B). Clusters of fibroblasts are often in close proximity to or attached to enzymatically fragmented collagen bundles. The fibroblasts themselves appear smaller than the malignant cells (cf. FIG. 1 C). The clusters of endothelial cells and also the clusters of fibroblasts sediment significantly more slowly than the clusters of malignant cells.

With the help of conventional immunochemical methods known in the prior art, those skilled in the art can detect the cellular homogeneity or at least almost near homogeneity of both the resulting colonies of malignant cells as well as those of stromal cells, i.e., the endothelial cells and the fibroblasts, reliably or at least almost reliably after incubation in ECM plates and fixation (for example, for three days).

Most of the fractionated and unfractionated decomposition (digestion) products contain clusters of malignant cells and/or stromal cell clusters which are capable of forming colonies ex vivo even in the presence of 6000 nM cisplatin.

With this example it is demonstrated first of all that a partial collagenase digestion of lung malignant tumor tissue followed by a short mild hydromechanical treatment leads to the release of pre-existing cell clusters which consist either of malignant cells or of various types of stromal cells, and which can be separated easily and simply.

The results thus obtained in the sensitivity test with cisplatin also show that the isolated microscopically identified stromal cell clusters often have cisplatin resistance even in the absence of malignant cells; this resistance might be due to a corresponding gene expression.

Literature Cited:

Dietz A, Tschöp K, Wichmann G, Granzow C: Method and kit for the ex vivo evaluation of the response of a tumor to conditions to be tested. International Publication Number WO 2009/124997 A1

Dollner R, Granzow C, Helmke B M, Ruess A, Schad A, Dietz A: The impact of stromal cell contamination on chemosensitivity testing of head and neck carcinoma. Anticancer Res. 24:325-31 (2004)

Granzow C, Kopun M, Heuser M, Herth F, Becker H D: Chemoresistance of human lung tumor stromal cells. Amer. Assn. Cancer Res. 95th Annual Meeting Proc. Suppl., abstract LB-82 (2004)

Kerbel R S: A cancer therapy resistant to resistance. Nature 390: 335-6 (1997)

Potti A, Dressman H K, Bild A, Riedel R F, Chan G, Sayer R, Cragun J, Cottrill H, Kelley M J, Petersen R, Harpole D, Marks J, Berchuck A, Ginsburg G S, Febbo P, Lancaster J, Nevins J R.: Genomic signatures to guide the use of chemotherapeutics. Nat. Med. 12:1294-1300 (2006)

The invention claimed is:

1. A method for separating clusters of malignant cells and clusters of stromal cells of a malignant tumor tissue sample ex vivo, comprising the following steps in order:
   (a) purifying and mincing the malignant tumor tissue sample,
   (b) suspending the minced tissue in culture medium,
   (c) subjecting the suspension obtained in (b) to an exclusive treatment solely with collagenase for a partial collegenase digestion, wherein *Clostridium histolyticum* collagenase is used in a concentration of 200 CDU to 250 CDU per mL at approximately 36° C. to 37° C. for a period of approximately 4 to 5 hours,
   (d) centrifuging the collagenase decomposition product obtained in (c) to obtain a pellet,
   (e) separating the pellet obtained in (d) from the supernatant,
   (f) decomposing the pellet from (e) and resuspending the resulting decomposed matter in culture medium by an aspiration device, the resuspension step comprising aspirating, returning and sucking in again several times, and subsequently transferring the resuspension to a culture vessel, (g) analyzing the resuspension obtained in (f) with regard to at least one cell cluster with a microscope, wherein the at least one cell cluster can be identified either on the basis of its phase-optical appearance either as a cluster of malignant cells, or as a cluster of endothelial cells, or as a cluster of fibroblasts, and (h) separating the cell clusters identified in (g).

2. The method according to claim 1, wherein the collagenase used in step (c) is used in a concentration of approximately 230 CDU/mL.

3. The method according to claim 1, wherein in step (g) the resuspension is analyzed with regard to cell clusters of malignant cells and also with regard to cell clusters of fibroblasts and/or cell clusters of endothelial cells, and wherein the cell clusters identified are aspirated separately, and each type of clusters is transferred to a separate culture vessel.

4. The method according to claim 1, wherein in step (g) the resuspension is subjected to a density gradient centrifugation in a separation solution of sucrose polymer, where the clusters of malignant cells sediment at higher concentrations of the sucrose polymer than the clusters of fibroblast or of endothelial cells.

5. The method according to claim 1, wherein in step (g) the resuspension is transferred to a separation chamber for centrifugal elutriation and then elutriated, wherein the clusters of malignant cells collect at higher flow rates than the clusters of fibroblasts or the clusters of endothelial cells.

6. The method according to claim 1, wherein the method is a precursor method for a method for testing the sensitivity and possible resistance of the cells of a malignant tumor tissue sample ex vivo for a known chemotherapeutic and/or radiotherapeutic agent.

7. The method for testing the response of malignant cells of a malignant tumor tissue sample ex vivo for a known chemotherapeutic and/or radiotherapeutic agent, wherein the malignant tumor tissue sample is first subjected to a method according to claim 1, and only the clusters of malignant cells thereby identified are used in the method for evaluation/testing.

8. The method according to claim 7, wherein the method for testing comprises the following measures:
   i) transferring the identified clusters of malignant cells to containers with a coating of extracellular matrix components, plating them out on this coating and exposing them to the chemotherapeutic and/or radiotherapeutic agent,
   ii) analyzing the number of cells and/or the number of colonies, preferably after performing a cytokeratin staining,
   iii) wherein the cell culture medium used in steps i) and ii) contains less than 100 nmol of flavin per 1 liter and is free of phenol red,
   iv) and wherein steps i) and ii) are performed in the absence of light of wavelengths below 520 nm,
   v) determining the IC50 value for the chemotherapeutic or radiotherapeutic agent or for the combination of chemotherapeutic and radiotherapeutic agent.

9. A method for testing the growth-inhibiting effect of a known chemotherapeutic and/or radiotherapeutic agent on a malignant tumor tissue sample ex vivo, whereby the malignant tumor tissue sample is exposed to the chemotherapeutic and/or radiotherapeutic agent and then the number of cells and/or cell colonies is analyzed and finally the IC50 value of the chemotherapeutic or radiotherapeutic agent or the combination of chemotherapeutic and radiotherapeutic agent is determined, and wherein the malignant tumor tissue sample, before being exposed to the chemotherapeutic and/or radiotherapeutic agent, is decomposed into clusters of stromal cells and of malignant cells by a method according to claim 1, and only the clusters of malignant cells are incubated with the chemotherapeutic and/or radiotherapeutic agent and then analyzed with regard to the IC50 value of the agent used.

10. The method according to claim 3, wherein the separated clusters of endothelial cells are subjected to a method for testing for the effect of substances which inhibit angioneogenesis.

* * * * *